United States Patent [19]

Blumberg

[11] Patent Number: 4,939,149
[45] Date of Patent: Jul. 3, 1990

[54] RESINIFERATOXIN AND ANALOGUES THEREOF TO CAUSE SENSORY AFFERENT C-FIBER AND THERMOREGULATORY DESENSITIZATION

[75] Inventor: Peter M. Blumberg, Frederick, Md.

[73] Assignee: The United States of America as represented by the Department of Health and Human Services, Washington, D.C.

[21] Appl. No.: 261,627

[22] Filed: Oct. 24, 1988

[51] Int. Cl.$^5$ ............................................. A61K 31/12
[52] U.S. Cl. .................................................. 514/691
[58] Field of Search ....................................... 514/691

[56] References Cited

U.S. PATENT DOCUMENTS 4,716,179 12/1987 Hecker et al. .

OTHER PUBLICATIONS

Hergenhahn, M. et al., J. Cancer Res. Clin. Oncol., 1984; 108 (1): 98–109.
Schmidt, R. et al., Carcinogenesis, 1983; 4(1): 77–81.
Adolf, W. et al., J. Nat. Prod., May–Jun. 1982; 45(3): 347–54.
Driedger, P. E. et al., Cancer Res., May 1980; 40(5): 1400–4.
Hartley, J. A. et al., Cancer Res., Oct. 1985; 45(10): 4864–70.
Yamasaki, H. et al., Carcinogenesis, 1982; 3(8): 905–10.
Edwards, M. C. et al., Mol. Pharmacol., May 1983; 23(3): 703–8.
Chem. Abst., vol. 93 (1980)–106819j.

*Primary Examiner*—Stanley J. Friedman
*Attorney, Agent, or Firm*—Birch, Stewart, Kolasch & Birch

[57] ABSTRACT

The present invention relates to a method for desensitizing a subject animal, which comprises administering to the subject animal a therapeutically effective desensitizing amount of resiniferatoxin for desensitizing the subject animal to neurogenic inflammation, to chemically and thermally induced pain and to responses involving sensory afferent pathways sensitive to capsaicin and to responses involving the hypothalamic temperature control region, and a pharmaceutically acceptable carrier therefor.

11 Claims, 10 Drawing Sheets

RESINIFERATOXIN AND ANALOGUES THEREOF TO CAUSE SENSORY AFFERENT C-FIBER AND THERMOREGULATORY DESENSITIZATION

FIELD OF THE INVENTION

The present invention relates to the use of resiniferatoxin to desensitize a subject animal to neurogenic inflammation, to chemically and thermally induced pain, to responses involving sensory afferent pathways sensitive to capsaicin (e.g. sensory afferent C-Fibers) and to responses involving the hypothalamic temperature control region.

BACKGROUND OF THE INVENTION

The phorbol esters, together with the structurally related ingenol and resiniferonol esters, are diterpene derivatives from plants of the families Euphorbiaceae and Thymeleaceae (Evans, F. J. and Taylor, S. E. (1983) *Fortshr. d. Chem. organ. Naturst*, Vol. 44, pp. 1–99; Hecker, E. (1978) *In Carcinogenesis, Mechanisms of Tumor Promotion and Cocarcinogenesis* (T. J. Slaga, A. Sivak and R. K. Boutwell, Eds.), Vol. 2, pp. 11–48, Raven Press, N.Y.). The phorbol esters have been the objects of intense research interest due to their tumor promoting activity (Hecker, E. (1968) *Cancer Res.*, Vol. 28, pp. 2238–2349). More recently, the description of the role of the phorbol esters as modulators of protein kinase have been studied (Ashendel, C. L. (1985) *Biochim. Biophys. Acta*, Vol. 822, pp. 219–242; Blumberg, P. M. (1988) *Cancer Res.*, Vol. 48, pp. 1–8). These compounds are also potent irritants, and their isolation from natural sources has been guided by the activity of organic extracts of the plants in a mouse ear reddening assay (Hecker, E., Immich, H., Bresch, H. and Schairer, H.-U. (1966) *Z. Krebsforsch*, Vol. 68, pp. 366–374). Resiniferatoxin (RTX), a resiniferonol ester, was isolated from *Euphoribia resinifera, E. poissonii* and *E. unispina* on the basis of this activity (Hergenhahn, M., Adolph, W. and Hecker, E. (1975) *Tet. Lett.* Vol. 19, pp. 1595–1598; Evans, F. J. and Schmidt, R. J. (1976) *Phytochemistry*, Vol. 15, pp. 333–335).

For the phorbol esters, esterification of the exocyclic hydroxyl at C20 causes marked loss of activity (Hecker, E. (1978) *Carcinogenesis, Mechanisms of Tumor Promotion and Cocarcinogenesis*. Vol. 2, pp. 11–48, Raven Press, New York). RTX differs from the tumor promoting resiniferonol derivatives in that it is esterified at this position. Structure-activity analysis indicates that this substituent, 4-hydroxy-3-methoxyphenylacetate, plays an essential role in determining activity. (Adolph, W., Sorg, B., Hergenhahn, M. and Hecker, E. (1982) *J. Nat. Prod.*, Vol. 45, pp. 347–354; Schmidt, R. J. and Evans, F. J. (1979) *Inflammation*, Vol. 3, pp. 273–280). Capsaicin, the irritant component in fruit of various species of Capsicum, also possesses a 4-hydroxy-3-methoxyphenyl substituent which is critical for activity (Szolcsanyi, J. and Jancso-Gabor. A, (1975), *Arzneim-Forsch*, Vol. 25, pp. 1877–1881).

One well documented action of capsaicin is to produce a dramatic fall in body temperature (Jancso-Gabor, A., Szolcsanyi, J. and Jancso, N. (1970), *J. Physiol*, Vol. 208, pp. 449–459; Szikszay, M., Obal, F. Jr., and Obal, F. (1982) *Naunyn-Schmiedeberg's Arch. Pharmacol*, Vol. 320, pp. 97–100). The inventors have explored possible homology between these two classes of irritant compounds to determine if RTX has a role in thermoregulation and to compare these effects with those of capsaicin.

U.S. Pat. No. 4,716,179 by Hecker et al discloses the use of a non-irritating or slightly irritating and/or tumor promoting diterpene alcohol and of derivatives thereof as antineoplastic preparations. Resinferatoxin was found to have neither a curative nor a significant tumor-inhibiting effect in carcinomas.

SUMMARY OF THE INVENTION

The present invention relates to a method for desensitizing a subject animal which comprises administering to the subject a therapeutically effective desensitizing amount of resiniferatoxin for desensitizing the subject animal to neurogenic inflammation, to chemically and thermally induced pain, to responses involving sensory afferent pathways sensitive to capsaicin (e.g. sensory afferent C-Fibers) and to responses involving the hypothalamic temperature control region, and a pharmaceutically acceptable carrier therefor, Furthermore, the resiniferatoxin may be administered topically, subcutaneously, intraperitoneally or intravenously.

DETAILED DESCRIPTION OF THE INVENTION

Figure 1A:
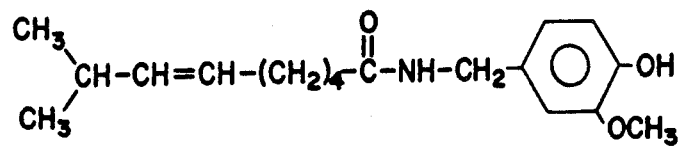
FIG. 1A shows the structure of capsaicin and FIG. 1B shows the structure for resiniferatoxin.

Resiniferatoxin (RTX) is a naturally occurring diterpene, structurally related to the phorbol esters, and was identified in the latex of 3 species of Euphorbia (*E. resinifera. E. poissonii,* and *E. unispina*) (Hergenhahn et al (1975) Tetrahedron Lett. 19, 1595–1598 and Schmidt et al (1976) Phytochemistry 15, 1778–1779). RTX was isolated on the basis of extraordinary activity in the mouse ear reddening assay (Hergenhahn et al (1975) Tetrahedron Lett. 19, 1595–1598), in which it exhibited 3 orders of magnitude greater potency than the most potent of the typical phorbol esters, phorbol 12-myristate 13-acetate (PMA) (Hecker, E. (1978) in Carcinogenesis, Mechanism of Tumor Promotion and Cocarcinogenesis, eds. Slaga, T. J., Sivak, A. and Boutwell, C. K. (Raven Press, New York), Vol. 2, pp. 11–48 and Adolph et al (1982) J. Nat. Prod. 45, 347–354). Characterization of RTX strongly suggested that its primary target was distinct from that of the phorbol esters. Unlike the persistent inflammation induced by the phorbol esters, the ear reddening induced by RTX was transient (Adolph et al (1982) J. Nat. Prod. 45, 347–354, Schmidt et al (1979) Inflammation 3, 273–280 and Hergenhahn et al (1982) J. Cancer Res. Clin. Oncol. 104, 31–39). RTX was not tumor promoting (zur Hausen et al (1979) Proc. Natl. Acad. Sci. U.S.A. 76, 782–785); RTX did not induce typical phorbol ester responses in cultured cell systems (zur Hausen et al (1979) Proc. Natl. Acad. Sci. U.S.A. 76, 782–785 and Driedger et al (1980) Cancer Res. 40, 1400–1404); and RTX did not efficiently compete for phorbol ester binding to protein kinase C (Driedger et al (1980) Proc. Natl. Acad. Sci. U.S.A. 77, 567–571).

A free 20-hydroxyl group is critical for phorbol ester activity (Hecker, E. (1978) in Carcinogenesis, Mechanism of Tumor Promotion and Cocarcinogenesis, eds. Slaga, T. J., Sivak, A. and Boutwell, C. K. (Raven Press, N.Y.), Vol. 2, pp. 11–48). RTX, in contrast, is esterified at this position with 4-hydroxy-3-methoxyphenylacetate, and this substituent has been shown to be essential for its unusual irritant activity (Adolph et al (1982) J. Nat. Prod. 45, 347–354 and Schmidt et al (1979) Inflammation 3, 273–280). Strikingly, a 4-hydroxyl-3-methoxyphenyl substituent is also a critical feature of capsaicin, the major pungent constituent of red pepper and other plants of the genus Capsicum (Jancso, N. (1968) in Pharmacology of pain (Pergamon Press, Oxford), Vol. 9, pp. 33–55 and Szolcsanyi et al (1975) Arzneim-Forsch. (Drug Res.) 25, 1877–1881) (See FIG. 1). Structure-activity analysis of capsaicin congeners, moreover, indicates that an ester linkage such as is found in RTX is adequately tolerated in place of the amide linkage present in the opposite orientation in capsaicin.

Capsaicin causes diverse physiological effects, of which pain, neurogenic edema, and hypothermia are prominent examples (Jancso, N. (1968) in Pharmacology of pain (Pergamon Press, Oxford) , Vol. 9, pp. 33–55, Szolcsanyi et al (1975) Arzneim-Forsch. (Drug Res.) 25, 1877–1881 and Buck et al (1986) Pharmacol. Rev. 38, 179–226). Acute response is followed by long-lasting desensitization. The postulated cellular mechanism is by transient activation followed by desensitization and, under some conditions, degeneration of C-fiber sensory afferent neurons (Jancso, N. (1968) in Pharmacology of pain (Pergamon Press, Oxford), Vol. 9, pp. 33–55, Buck et al (1986) Pharmacol. Rev. 38, 179–226 and Scadding, J. W. (1980) J. Anat. 131, 473–484). These neurons contain substance P and associated neuropeptides. The biochemical mechanism for this effect of capsaicin on C-fibers is not known.

The inventors have confirmed the possible homology of RTX and capsaicin (i.e. both compounds produced a dramatic fall in body temperature in mice followed by cross-tolerance (deVries et al (1988) submitted, Life Sciences) and have now compared the potencies and in vivo activities of RTX and capsaicin in detail, as discussed hereinbelow.

Accordingly, the inventors have characterized a commercially available but largely unstudied natural product, resiniferatoxin. RTX qualitatively resembles capsaicin in its activity, but differs quantitatively in potency (i.e. $10^3$–$10^4$ fold more potent) and in relative spectrum of actions. Resiniferatoxin thus causes desensitization to neurogenic inflammation, to chemically and thermally induced pain, and to responses involving sensory afferent pathways including C-fibers and the hypothalamic temperature control region. The induced desensitization may have application in arthritis, asthma, allergic responses, fever, pain associated with cancer or Herpes virus infection, and in biological processes mediated by substance P or other neuropeptides depleted by capsaicin treatment.

As indicated above, resiniferatoxin has similar effects to capsaicin, but differs in its much greater potency—up to $10^4$, which should remarkably reduce side effects and permit easier application (i.e. smaller volume or absorption through inefficient routes). RTX also shows a somewhat different spectrum of action, enabling greater desensitization at a given level of systemic toxicity and greater desensitization relative to acute induction of pain.

Moreover, desensitization by resiniferatoxin can be activated by topical, intravenous, intraperitoneal, and subcutaneous administration. RTX may be administered to an animal such as a mammal (e.g. mouse, rat or human).

Furthermore, it should be noted that capsaicin exerts its actions on all mammals examined, but not on birds and lower vertebrates (Monsereenusorn et al (1982) CRC Crit. Rev. Toxicol. 10, 321–339). Based on the resemblances in the activities of capsaicin and resiniferatoxin documented in this application, we extrapolate that the effects of resiniferatoxin are not limited to rats and mice but extend to man as well.

Resiniferatoxin, an extremely irritant diterpene present in several members of the genus Euphorbia, produced an 8° C. decrease in the rectal temperature of mice with an effective dose in the range of 2–20 μg/kg. The structurally related natural product capsaicin produced a similar magnitude of fall in body temperature albeit with 1000-fold lower potency. Tolerance to the hypothermic effects of both drugs developed readily and cross-tolerance between drugs was observed. The extreme potency of resiniferatoxin should facilitate biochemical analysis of the mechanism of action of this class of compounds.

RTX was remarkable for its potency in the mouse ear reddening assay. Its 50% effective dose, $1.6 \times 10^{-14}$ moles/ear, indicated a 1000-fold greater potency than that of the most active of the typical phorbol esters, phorbol 12-myristate 13-acetate. (Adolf, W., Sorg, B., Hergenhahn, M. and Hecker, E. (1982) J. Nat. Prod., Vol. 45, pp. 347–354).

Although the mechanism of action of RTX has not been extensively studied, its mechanism is clearly distinct from that of the phorbol esters for the following reasons:

(1) Whereas phorbol esters cause comparable ear reddening at 3 and at 24 hours after application, the irritant activity of RTX is only found at the earlier time point (Adolf, W. et al (1982) J. Nat. Prod., Vol. 45, pp. 347–354; Schmidt, R. J. et al (1979). Inflammation. Vol. 3, pp. 273–280; Hergenhahn, M., et al (1982) J Cancer Res. Clin. Oncol., Vol. 104, pp. 31–39.

(2) RTX is not tumor promoting and is much less potent than typical phorbol esters at eliciting responses in a range of cultured cells. (zur Hausen, H., Bornkamm, G. W., Schmidt, R. and Hecker, E. (1979) Proc. Natl. Acad. Sci. U.S.A., Vol. 76, pp. 782–785; Driedger, P. E. and Blumberg, P. M. (1980) Cancer Res., Vol. 40, pp. 1400–1404).

(3) RTX does not compete for phorbol ester binding sites on protein kinase C. (Driedger, P. E. and Blumberg, P. M. (1980) Proc. Natl. Acad. Sci. U.S.A., Vol. 77, pp. 567–571).

RTX, the active ingredient of the present invention, can be made into pharmaceutical compositions by combination with appropriate medical carriers or diluents. For example, RTX can be dissolved in oils, propyleneglycol or other solvents commonly used to prepare injectable solutions. Suitable carriers include physiological saline, polyethylene glycol, ethanol, sesame oil, cremophor and isopropyl myristate. For topical application, RTX can be formulated as an ointment or cream.

The following methods and excipients are merely exemplary and in no way limit the invention.

The compounds of the present invention in pharmaceutical dosage forms may be used in the form of their pharmaceutically acceptable salts, and also may be used alone or in appropriate association, as well as in combination with other pharmaceutically active compounds.

The compounds of the present invention may be formulated into preparations for injections by dissolving, suspending or emulsifying them in aqueous solvents such as normal saline, Dextrose 5%, or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds of the invention may be combined with other compounds having the desired effect.

The desirable dose of the compounds of the present invention varies with the subject, drug form, method and period of administration. However, in order to obtain desirable effects, generally it is recommended to administer $0.1\times10^{-3}$ to $5\times10^{-2}$ mg/kg, preferably $0.1\times10^{-3}$ to $5\times10^{-3}$ mg/kg, body weight of the compounds of the present invention for single application, or less upon multiple application. In terms of composition, compounds should be present between. 0.0001 to 10% by weight, preferably 0.0001 to 1% by weight.

Accordingly, the following experiments demonstrate that resiniferatoxin is an extremely irritant diterpene present in the latex of several members of the genus Euphorbia. Its mechanism of action is clearly distinct from that of structurally related phorbol esters. Since RTX possesses a 4-hydroxy-3-methoxyphenyl substituent, a key feature of capsaicin, the major pungent ingredient of plants of the genus Capsicum, the ability of RTX to induce typical capsaicin responses is examined. The treatment of rats with RTX (Example 1), like treatment with capsaicin, causes hypothermia, neurogenic inflammation and pain. These responses are followed by loss of thermoregulation, by desensitization to neurogenic inflammation, and by chemical and thermal analgesia, with cross-tolerance between RTX and capsaicin. RTX is 3-4 orders of magnitude more potent than capsaicin for the effects on thermoregulation and neurogenic inflammation. RTX is only comparable in potency to capsaicin, however, the assays for induction of acute pain, and the desensitization to acute pain appears to require less RTX than did desensitization for the other responses. Thus, RTX acts as an ultrapotent capsaicin analog and may distinguish between subclasses of capsaicin response.

The following Examples are intended to illustrate the claimed invention and will enable others skilled in the art to understand the invention more completely. However, the invention should not be interpreted as being limited to only these representative examples.

EXAMPLE 1

Methods

Sprague-Dawley rats (females, 250–300 g) are purchased from the Zivic-Miller Laboratories, (Zelienople, Pa.). Animals are allowed access to food and water ad libitum through the course of the experiments. The numbers of animals used in different experimental groups are indicated in the legends to 1–3 tables and FIGS. 1-10. RTX (MW 628) is obtained from Chemicals for Cancer Research, Inc. (Chanhassen, Minn.), and Capsaicin (MW 305) from Polysciences (Warrington, Pa.). The compounds are administered in 10% ethanol/ 10% Tween-80/ 80% physiological saline solution unless otherwise indicated.

Pain-Inducing Potency

Acute pain-inducing potency of the compounds is assessed as described by Jancso et al (Jancso et al (1961) Acta Physiol. Acad. Sci. Hung. 19, 113–131), which is herein incorporated by reference. Briefly, solutions at ten-fold increasing concentrations of compound in physiological saline are dropped into the eyes of rats and the number of protective movements (eye-wipings with the foreleg) is determined. To minimize the irritant being rinsed out by lacrimation, the instillation is repeated once. The solution by itself induced no wipings. The concentrations inducing an equal reaction of 10 wipings (moderate pain-producing potency) is calculated from the dose-response curves (Szolcsanyi et al (1975) Arzneim-Forsch. (Drug Res.) 25, 1877–1881). Except for these experiments, both RTX and capsaicin are applied under light ether anesthesia to avoid unnecessary pain.

Analysis of Vascular Permeability

Changes in vascular permeability to serum albumin are analyzed using the Evan's blue technique (Saria et al (1983) J. Neurosci. Meth. 8, 41–49). From 8–12 rats at each time point and dose are anesthetized with pentobarbitone (40 mg/kg), the right jugular vein is exposed, and 20 mg/kg of Evan's blue (1% Evan's blue solution in physiological saline containing 100 IU/ml heparin) is injected (Saria et al (1983) J. Neurosci. Meth. 8, 41–49). At the indicated times (e.g. typically 30 minutes unless otherwise indicated) after injection, the animals are killed and the tissues (e.g. skin, lung, ovary, stomach, intestine) excised. The excised tissues are blotted with filter paper to remove excess fluid, immediately weighed, and then placed in 4.0 ml formamide for 24 hours at 50° C. to extract the Evan's blue. Evan's blue is quantitated by determining absorption at 620 nm in a Shimadzu spectrophotometer.

Extent of Edema

The extent of edema is measured by treating the hind paw with the irritant or solvent. At the indicated time (e.g. 30 minutes) the animal is killed, 1 cm diameter skin punches are removed and quickly weighed, and after drying for 24 hours at 50° C. the skin punches are reweighed. The difference in the water content between irritant-and solvent-treated animals represents the extent of edema (Fischer et al (1988) Cancer Res. 48, 659–664).

To obtain direct evidence for the neurogenic origin of the observed inflammation, from 10–14 denervated rats are purchased from Zivic-Miller Laboratories. Determination of edema in response to RTX and is carried out 3 days after the left saphenous nerve had been cut in the upper thigh (Jancso et al (1967) Br. J. Pharmacol. Chemother. 31, 138-151). Irritants are applied on both hind paws; the right intact paw serves as a positive control.

Body Temperature

The body temperature of the rats are determined as described by Szikszay et al (1982) Naunyn-Schmiedeberg's Arch. Pharmacol. 320, 97-100. Rats are habituated prior to treatment to the room temperature (20° C.) and to the small-animal temperature probe (Cole-Parmer, Chicago, Ill.) which is introduced rectally to a depth of 5 cm.

Desensitization against acute chemical pain is examined using the eye-wiping test. RTX is injected subcutaneously and 4 hours later capsaicin is instilled into the eye. Antinociceptive effect against chronic pain is tested by the method of Dubuisson et al (1977) Pain 4, 161-174. 5% formalin solution is injected under the plantar surface of the right forepaw 4 hours after topical RTX or capsaicin administration. Behavior of animals is scored as described in Dubuisson et al (1977) Pain 4, 161-174 during an observation period of 60 minutes. Heat nociception is examined in the tail-immersion test at 50° C. (D'Amour et al (1941) J. Pharmacol. Exp. Ther. 72, 74-79 and Gamse, R. (1982) Naunyn-Schmiedeberg's Arch. Pharmacol. 320, 205-216). Desensitization against the inflammatory response is determined by measuring extravasated Evan's blue after a high paw has been painted with xylene, an effective inducer of neurogenic inflammation (Jancso et al (1967) Br. J. Pharmacol. Chemother. 31, 138-151). Desensitization is also determined by measuring extravasated Evan's blue after dextran is injected under the hind paw skin (25 ug in a volume of 50 ul); dextran releases vasoactive substances without causing neurogenic inflammation (Jancso et al (1967) Br. J. Pharmacol. Chemother. 31, 138-151).

Results

Capsaicin has profound effects on thermoregulation in mammals (Jancso-Gabor et al (1970) J. Physiol. (Lond.) 206, 495-507, Virus et al (1979) Life Sci. 25, 1273-1284, Monsereenusorn et al (1982) CRC Crit. Rev. Toxicol. 10, 321-339 and Yaksh et al (1979) Science (Wash. D.C.) 206, 481-483). RTX, like capsaicin, causes a 2°-3° C. drop in rectal temperature 1 hour after treatment of rats maintained at 20° C. (See FIG. 2). The $ED_{50}$ for RTX is $3 \times 10^{-7}$ g/kg, compared to an $ED_{50}$ for capsaicin of $2 \times 10^{-3}$ g/kg.

Repeated treatment with capsaicin causes complete desensitization to its hypothermic effects (Jancso, N. (1968) in Pharmacology of pain (Pergamon Press, Oxford), Vol. 9, pp. 33-55 and Yaksh et al (1979) Science (Wash. D.C.) 206, 481-483). Similarly, treatment with RTX at a dose of $1 \times 10^{-4}$ g/kg causes an abrupt decrease in body temperature which largely returns to control levels after 3 hours (See FIG. 3A). A second treatment with RTX causes only a limited response and further treatments have no effect. The desensitized animals show cross-desensitization to capsaicin ($10^{-2}$ g/kg), whereas control animals show marked hypothermia to capsaicin.

Capsaicin desensitized rats display an inability to adapt to heat stress (Jancso, N. (1968) in Pharmacology of pain (Pergamon Press, Oxford), Vol. 9, pp. 33-55 and Virus et al (1979) Life Sci. 25, 1273-1284). If subjected to elevated ambient temperature (38° C.), RTX-desensitized rats show a steady rise in body temperature, ultimately leading to collapse, in contrast to control animals (See FIG. 3B).

Desensitization with capsaicin can be achieved either by means of a single large dose or of repeated incremental doses (Jancso, N. (1968) in Pharmacology of pain (Pergamon Press, Oxford), Vol. 9, pp. 33-55 and Buck et al (1986) Pharmacol. Rev. 38, 179-226). The former procedure is more convenient for quantitation and comparison. Therefore, the dose dependency was determined for desensitization to RTX-induced hypothermia following pretreatment with a single, subcutaneous injection of RTX (See FIG. 4). The dose response curve was extremely steep and yielded an $ED^{50}$ of $5 \times 10^{-6}$ g/kg. This value is approximately an order of magnitude greater than the $ED_{50}$ for the direct hypothermic effect, but similar to that which gives a maximal response.

Induction of neurogenic inflammation is a second prominent feature of the capsaicin response (Jancso et al (1967) Br. J. Pharmacol. Chemother. 31, 138-151, Virus et a) (1979) Life Sci. 25, 1273-1284 and Monsereenusorn et al (1982) CRC Crit. Rev. Toxicol. 10, 321-339). Inflammation was quantified by measuring extravasation of Evan's blue dye. Like capsaicin, RTX applied topically to the hind paw of rats causes dramatic extravasation. The $ED_{50}$ for topical administration of RTX is $3 \times 10^{-5}$ g/paw, compared to an $ED_{50}$ for capsaicin of $3 \times 10^{-2}$ g/paw (See FIG. 5). The kinetics of edemas formation are determined from the water content of the hind paw skin as a function of time. No edema formation is observed up to 30 minutes; the water content reaches its peak at 90 minutes; and the edema disappears by 4 hours (See FIG. 7). The solvent acetone by itself did not have any effect.

Since the inflammation caused by capsaicin is neurogenic, the inflammatory response thereof is compared to RTX in intact paws and in paws which have been denervated by transection of the saphenous nerve in the thigh of the rat. Denervation totally blocks the inflammatory response to RTX, measured either by Evan's blue extravasation or by increase in water content as shown in Table 1 below.

TABLE 1

| Effect of Denervation on RTX-induced Edema | |
|---|---|
| Treatment | Extravasated Evan's Blue ng/mg tissue |
| solvent only | 11.31 ± 2.49 |
| 80 ug RTX on denervated paw | 8.86 ± 1.36 |
| 80 ug RTX on intact paw | 84.22 ± 11.35 |
| | Water content of skin, % |
| solvent only | 65.1 |
| 50 ug RTX on denervated paw | 64.9 |
| 50 ug RTX on intact paw | 71.6 |

The left saphenous nerve is cut 3 days before the experiment. Irritant is applied topically in 50 ul acetone on both hind paws; the intact paw serves as a positive control. Values are the mean ±SEM standard error of the mean for 10-14 animals in 2 experiments.

Although Evan's blue extravasation is quantified only following topical treatment of the paw with RTX, visual examination of systematic extravasation after intravenous injection of RTX was performed (0.1 ug/kg). RTX induces a similar pattern of extravasation to that reported for capsaicin (Saria et al (1983) Naunyn-Schmiedeberg's Arch. Pharmacol. 324, 212-218): extravasation in skin, lung, ovary, and most other tissues, but characteristically not in stomach and intestine.

Capsaicin treatment is followed by desensitization to neurogenic inflammation (Jancso, N. (1968) in Pharmacology of pain (Pergamon Press, Oxford), Vol. 9, pp. 33–55, Buck et al (1986) Pharmacol. Rev. 38, 179–226, Virus et al (1979) Life Sci. 25, 1273–1284 and Monsereenusorn et al (1982) CRC Crit. Rev. Toxicol. 10, 321–339). Injection of RTX subcutaneously likewise prevents Evan's blue extravasation upon challenge 4 hours later with either RTX or capsaicin as shown in Table 2 below. RTX pretreatment similarly blocks response to xylene, another potent neurogenic irritant (Jancso et al (1967) Br. J. Pharmacol. Chemother. 31, 138–151), but has little effect on the response to dextran, a potent irritant with a non-neurogenic mechanism.

TABLE 2

Specificity of RTX-Desensitization

| Treatment | Evan's blue extravasation* % of control |
| --- | --- |
| xylene (50 ul/paw) | 14.4 |
| capsaicin (20 mg/paw) | 12.6 |
| RTX (50 ug/paw) | 3.5 |
| * dextran (25 ug in 50 ul saline) | 118 |

RTX (300 ug/kg) is injected under the back skin. Controls are injected with vehicle alone. 4 hours later xylene, capsaicin, or RTX is painted on the skin of the hind paw or dextran is injected under the skin. Evan's blue extravasation is determined 10 minutes after xylene or dextran treatment and 30 minutes after capsaicin or RTX treatment. Values are the mean for 8–10 animals in 2 experiments.

The desensitization induced by subcutaneously injection of RTX is rapidly expressed and of long duration. Inhibition of neurogenic inflammation is greater than 70% by 1 hour and achieves a level plateau by 4 hours which is maintained over the next 4 days. Responsiveness only partially returns by 7 days after treatment.

Figure 4:
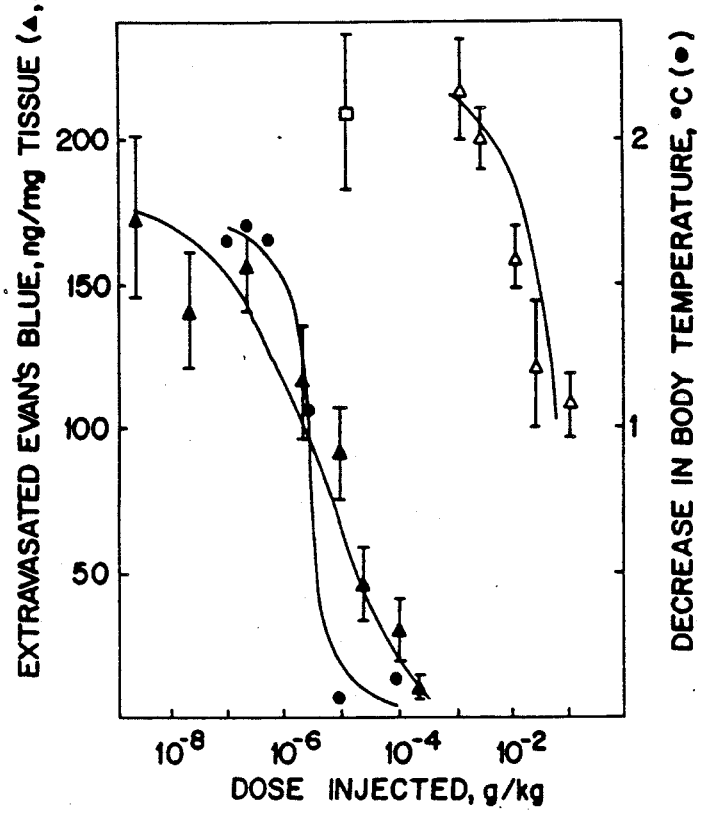
FIG. 4 shows the dose dependence of desensitization to hypothermic action and Evans blue extravasation.

The $ED_{50}$ for inhibition of xylene-induced Evan's blue extravasation by subcutaneous injection of RTX is $5 \times 10^{-6}$ g/kg (See FIG. 4). Similarly, $ED_{50}$ for inhibition of xylene-induced Evan's blue extravasation by subcutaneous injection for capsaicin is $10^{-1}$ g/kg. In the case of capsaicin, the maximum tolerated subcutaneous dose affords only partial desensitization upon a single administration, whereas complete desensitization is attainable with RTX.

Capsaicin potently stimulates chemogenic pain receptors (Jancso, N. (1968) in Pharmacology of pain (Pergamon Press, Oxford), Vol. 9, pp. 33–55 and Monsereenusorn et al (1982) CRC Crit. Rev. Toxicol. 10, 321–339), and the irritancy to the eye has been utilized most extensively to quantitate capsaicin structure-activity relations (Szolcsanyi et al (1975) Arzneim-Forsch. (Drug Res.) 25, 1877–1881 and Jancso et al (1961) Acta Physiol. Acad. Sci. Hung. 19, 113–131). As in the other assays (e.g. described above), RTX proves to be more potent than capsaicin (See FIG. 6A). However, the difference in potency is much less than the $10^3-10^4$-fold difference observed for the hypothermic and inflammatory effects. In addition, a latency period of 5–10 seconds is observed for RTX treatment compared to an immediate response upon capsaicin instillation, and the duration of the response is longer. Extension of the dose response curves for the eye wiping response to higher levels is not carried out so as to avoid undue pain.

Injection of RTX subcutaneously causes desensitization of the eye wiping response to capsaicin. The $ED_{50}$ for RTX is $1 \times 10^{-7}$ g/kg, a dose significantly less than that for desensitization to the hypothermic and inflammatory effects. This difference is confirmed in animals treated with RTX at $1 \times 10^{-6}$ g/kg and assessed for both the eye wiping response and Evan's blue extravasation.

RTX desensitization to chemical and thermal nociception is also examined in two other standard assays such as (i) response to formalin injection into the forepaw (Dubuisson et al (1977) Pain 4, 161–174 and Hayes et al (1981) Neuropharmacol 20, 505–511) and (ii) tail immersion into 50° C. water (D'Amour et al (1941) J. Pharmacol. Exp. Ther. 72, 74–79 and Gamse, R. (1982) Naunyn-Schmiedeberg's Arch. Pharmacol. 320, 205–216). RTX blocks nociception in both cases and does so with greater potency than does capsaicin as shown in Table 3 below.

TABLE 3

Effect of RTX Pretreatment on Sensory Functions

| Pretreatment[a] | Pain index[b] | Latency time[c] (sec) |
| --- | --- | --- |
| Solvent only | 3.0 | 6.8 ± 1.3 |
| RTX, 1 ug/paw | 3.0 | 7.2 ± 1.3 |
| RTX, 10 ug/paw | 1.5 | 6.0 ± 1.0 |
| RTX, 100 ug/paw | 0.2 | 42.0 ± 9.3 |
| capsaicin, 3 mg/paw | 0.2 | 19.4 ± 8.1 |

Discussion

The data strongly suggests that RTX functions as a capsaicin analog. RTX induces each of the three characteristic acute physiological responses to capsaicin which are examined—hypothermia, neurogenic inflammation, and pain. The acute response to RTX is followed by desensitization, a typical feature of capsaicin but not of unrelated irritants. The RTX-desensitized animals, moreover, displays cross-tolerance to capsaicin.

Although RTX mimicks capsaicin in its qualitative action, quantitatively it differs drammatically in potency. RTX is much more potent than capsaicin for induction of hypothermia ($7 \times 10^3$-fold, administered subcutaneously), for induction of neurogenic inflammation ($1 \times 10^3$-fold, applied topically), and for desensitization of neurogenic inflammation ($2 \times 10^5$-fold, administered subcutaneously). In studies in the mouse, (Example 2 below), RTX is also found to be $2 \times 10^3$-fold more potent for induction of hypothermia.

In addition to being more potent than capsaicin as demonstrated by the above assays, RTX also displays a different spectrum of action. The potency of RTX in the eye wiping assay, a measure of acute pain, is within a factor of 2 of that of capsaicin, in contrast to the $10^3-10^5$-fold difference described above. For desensitization of neurogenic inflammation, a single dose of RTX affords complete desensitization, whereas the maximum tolerated dose of capsaicin causes only partial desensitization. This qualitative difference may reflect different relative toxicities upon subcutaneous administration. The maximum tolerated dose of RTX is approximately 100-fold its $ED_{50}$ for desensitization of neurogenic inflammation, whereas the $ED_{50}$ for capsaicin is the maximum tolerated dose. Although differences in pharmacokinetics may explain some of the disparities in relative potencies, it seems unlikely to account for the differences of 105-fold which are observed.

Comparison of the potencies of RTX for desensitization in the eye wiping and Evans blue extravasation responses also imply heterogeneity of action. Desensitization in the eye-wiping assay is achieved with a 100-fold lower dose of RTX than in the latter assay, although desensitization with RTX is carried out in the same fashion in both cases and indeed both responses could be assessed in the same animals.

A previous investigation of capsaicin and related analogs likewise suggests different patterns of responses for different congeners. Whereas capsaicin causes both acute irritation and long lasting desensitization, zingerone, the pungent ingredient in ginger, lacks desensitizing activity (Jancso, N. (1968) in Pharmacology of pain (Pergamon Press, Oxford), Vol. 9, pp. 33–55). It has been suggested that the acylamide linkage, which is present in capsaicin but missing in zingerone, might be essential for desensitization (Jancso, N. (1968) in Pharmacology of pain (Pergamon Press, Oxford), Vol. 9, pp. 33–55). The high desensitizing potency of RTX argues against this suggestion.

RTX represents a powerful new tool for probing mechanisms of pain, neurogenic inflammation, and thermoregulation. Its high potency should facilitate receptor analysis; its structural relationship to the phorbol-related diterpenes affords a new family of derivatives to define the capsaicin pharmacophore. Given the potential therapeutic implications of C-fiber desensitization, the unique spectrum of action of RTX is of particular interest.

The figures of Example 1 are discussed in greater detail hereinbelow.

Figure 1B:
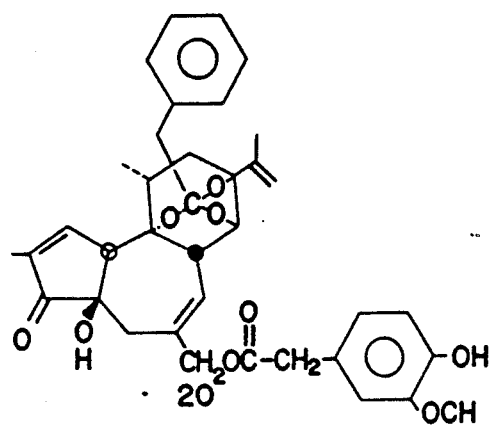

FIG. 1A shows the structure of capsaicin and FIG. 1B shows the structure for resiniferatoxin.

Figure 2:
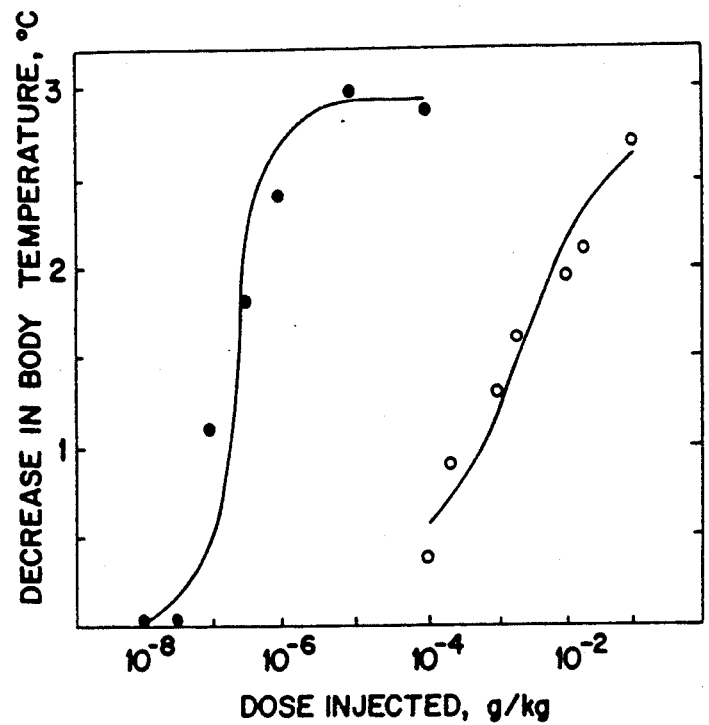
FIG. 2 shows the induction of hypothermia in rats by RTX or capsaicin.

FIG. 2 shows the induction of hypothermia in rats by RTX or capsaicin. The fall in rectal temperature is measured 1 hour after the subcutaneous injection of RTX (●) or capsaicin (o) at the indicated doses. Points represent the mean for 10 animals in 2 experiments.

Figure 3:
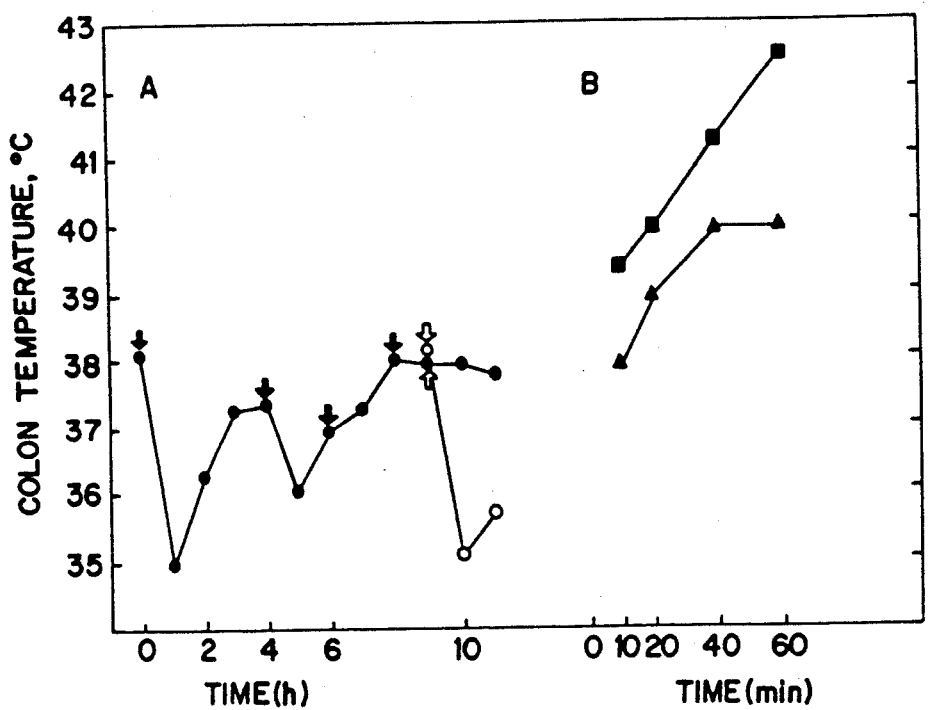
FIG. 3 shows the body temperature of rats as a function of time after the administration of RTX.

FIG. 3 shows the body temperature of the rats as a function of time after administration of RTX.

(A) Animals are injected with 100 ug/kg of RTX at the times indicated by the solid arrows (●). Cross-tolerance is examined by injection of 10 mg/kg capsaicin (open arrows). Vehicle controls are injected with the same dose of capsaicin (o). Values are the mean for 6-8 animals in 2 experiments.

(B) Vehicle controls (▲) or animals desensitized by subcutaneous injections with a cumulative dose of 400 ug/kg RTX (■) are exposed to high ambient temperature (38° C.). Hypothermia results in collapse of the rats. Values are the mean for 8 animals in two experiments.

FIG. 4 shows the dose dependence of desensitization to hypothermic action and Evans blue extravasation. Extravasation is induced by xylene (50 ul/paw) 4 hours after RTX (▲) or capsaicin (Δ) is injected subcutaneously at the indicated doses. Values are the mean±SEM for 8-12 animals in 3 experiments. □ represents xylene-induced Evans blue extravasation in vehicle controls. Hypothermia is induced by injection of 100 g/kg RTX, a dose providing a maximal response, 12 hours after RTX pretreatment (●) at the indicated doses. The time interval is chosen to avoid any interference between hypothermia produced by the pretreatment and the test dosage. Values are the mean for 8-10 animals in 2 experiments.

Figure 5:
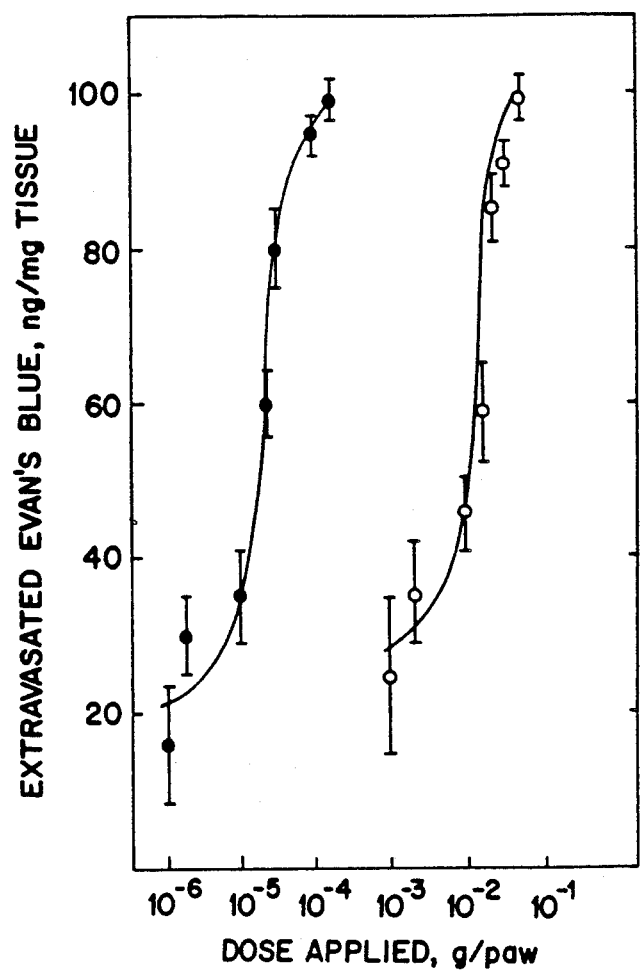
FIG. 5 shows the dose dependence of Evans blue extravasation induced by topical RTX or capsaicin.

FIG. 5 shows the dose dependence of Evans blue extravasation induced by topical RTX or capsaicin. RTX (●) or capsaicin (o) at the indicated doses is painted on the skin of the hind paw in 50 ul acetone. Extravasation is measured 30 minutes after application. Points are the mean ±SEM for 10 animals in 2 experiments.

Figure 6:
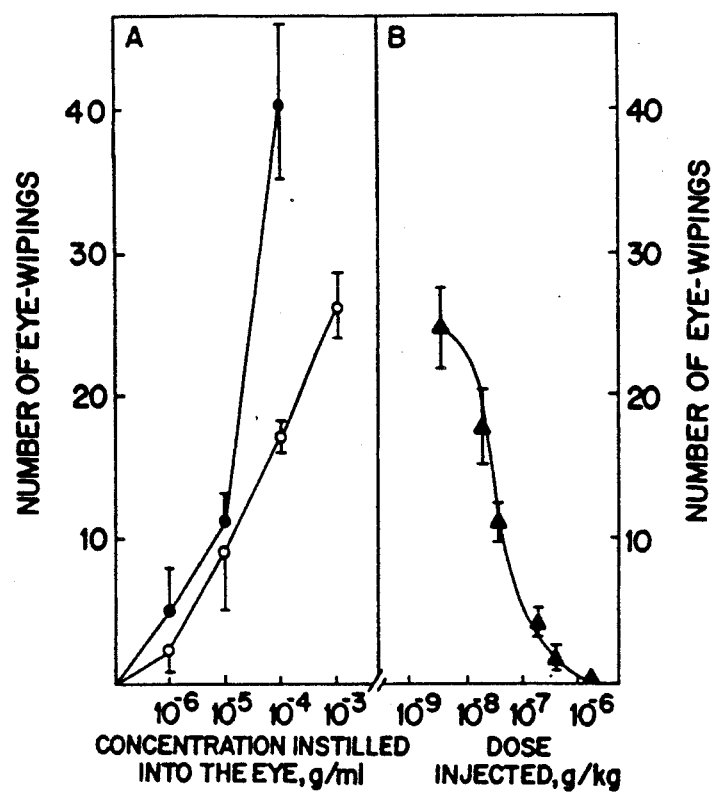
FIG. 6 shows the dose dependence of eye wiping in rats in response to instillation of RTX or capsaicin.

FIG. 6 shows the dose dependence of eye wiping in response to instillation of RTX or capsaicin.

(A) RTX (●) or capsaicin ( 0 ) solutions at the indicated concentrations is instilled into the eyes of rats. Each value is the mean ±SEM for 12 animals in 3 experiments.

(B) Animals are treated by subcutaneous injection of RTX at the indicated doses and the eye-wiping response to $10^{-3}$ g/ml capsaicin is determined 6 hours later. Values are the mean ±SEM for 8-10 animals in 2 experiments.

Figure 7:
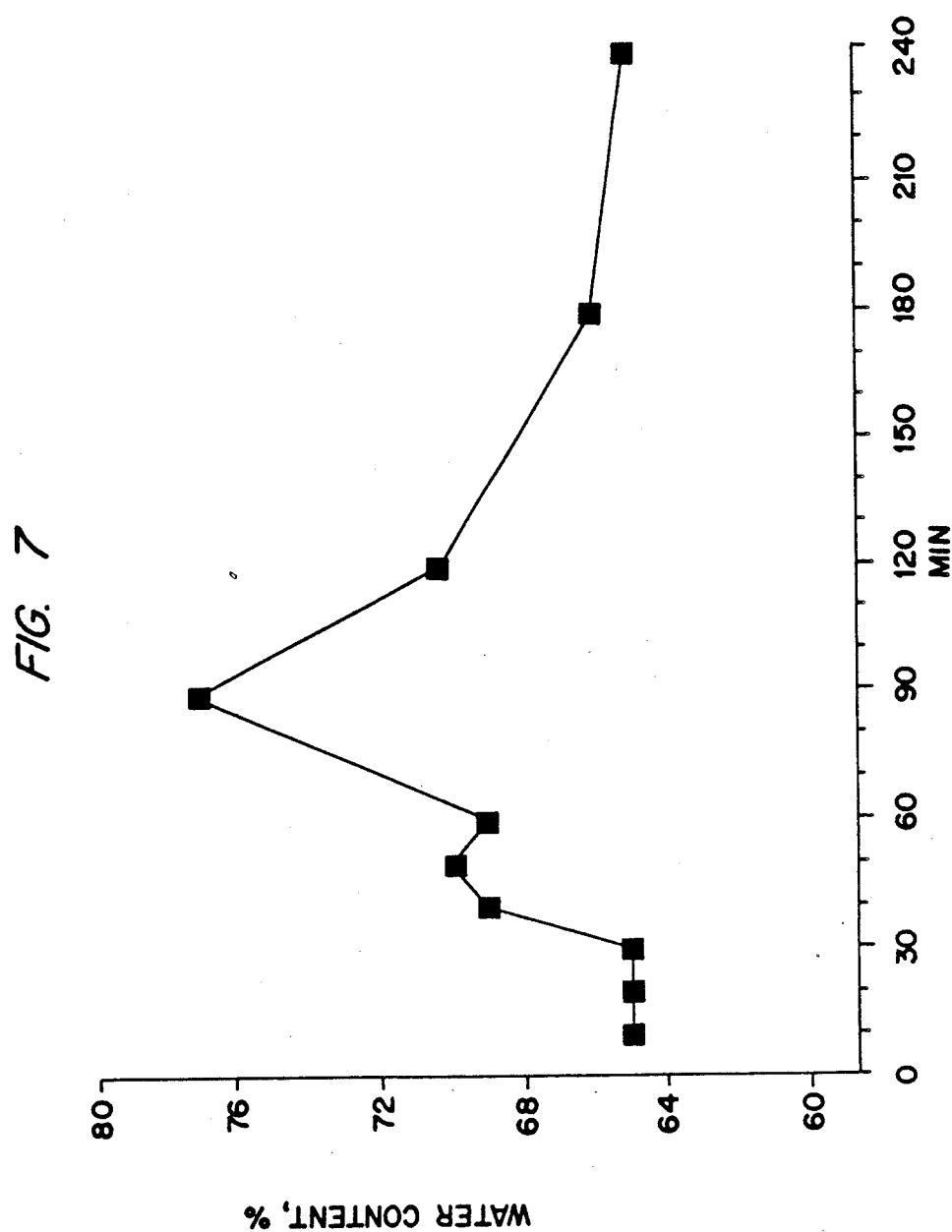
FIG. 7 shows the water content of the hind paw skin of rats after RTX treatment.

FIG. 7 shows the water content of the hind paw skin of rats after RTX treatment. Resiniferatoxin, 50 ug, was applied to the hind paw skin of rats and the water content of the skin was measured at the illustrated times, ranging between 10 minutes and 4 hours. Points represent the average values from 5 animals at each time of application. The experiment was repeated once and gave the same results.

EXAMPLE 2

Materials and Methods

Body temperature of the mice is determined essentially as described by Obal and coworkers. (Szikszay, M., Obal, F. Jr. and Obal, F. (1982) *Naunyn-Schmiedeberg's Arch. Pharmacol.*, Vol. 320, pp. 97–100).

From 10–36 female CD-1 mice, 25–30 g, are habituated prior to treatment to both the experimental room (22°–23° C.) and to the small-animal temperature probe (Cole-Parmer, Chicago, Il.) which is introduced rectally to a depth of 2.5 cm. Drugs are prepared in 10% ethanol/10% Tween-80/80% phosphate buffered saline and administered in volumes of less than 0.1 ml at the indicated doses of 0.2–40 ug/kg of resiniferatoxin or 2–15 mg/kg of capsaicin. Animals are allowed free access to food and water through the course of the experiments.

Dose response curves are analyzed by the curve-fitting program KA (McPherson, G. A., Molenaar, P., Raper, C. and Malta, E. (1983) *J. Pharmacol. Methods*, Vol. 10, pp. 231–241).

Resiniferatoxin (M.W. 628) was obtained from Chemicals for Cancer Research (Chanhassen, Minn.) and capsaicin (M.W. 305) from Polysciences (Warrington, Pa.).

Results

Figure 8:
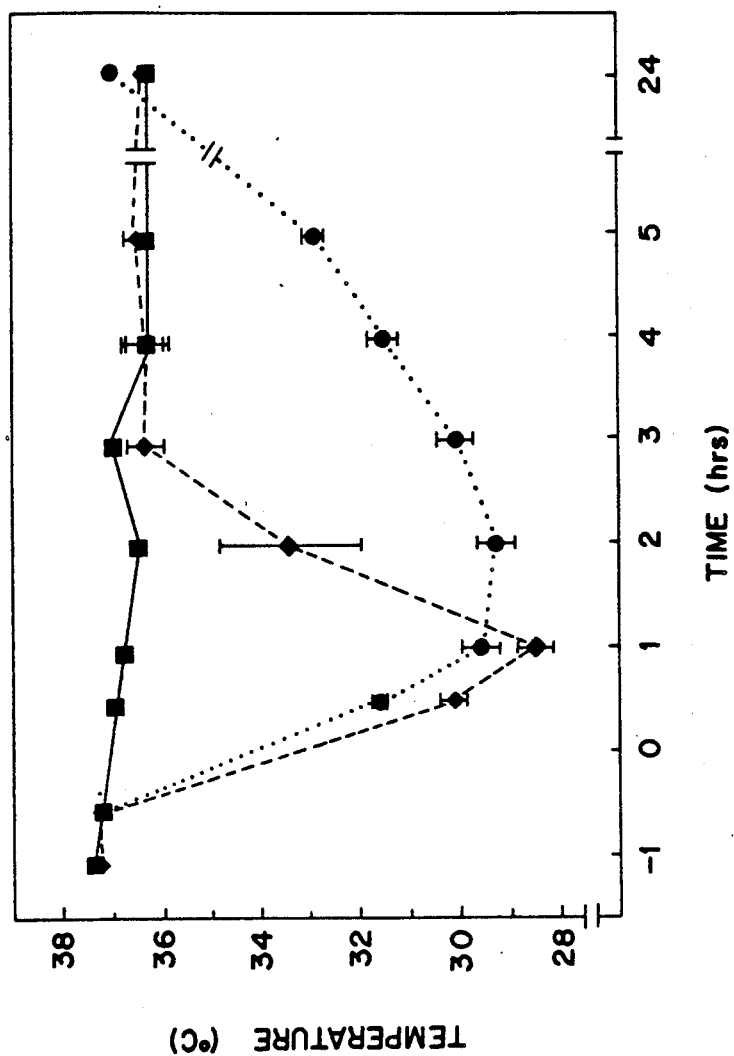
FIG. 8 shows the body temperatures of the mice.

Capsaicin (15 mg/kg) produces a profound drop in the body (rectal) temperature of mice upon subcutaneous injection as shown in FIG. 8. The effect is maximal at 1 hour and returns to baseline by 3 hours. RTX (20 g/kg) causes a comparable drop in body temperature. However, the duration of action of RTX is several-fold longer.

Figure 9:
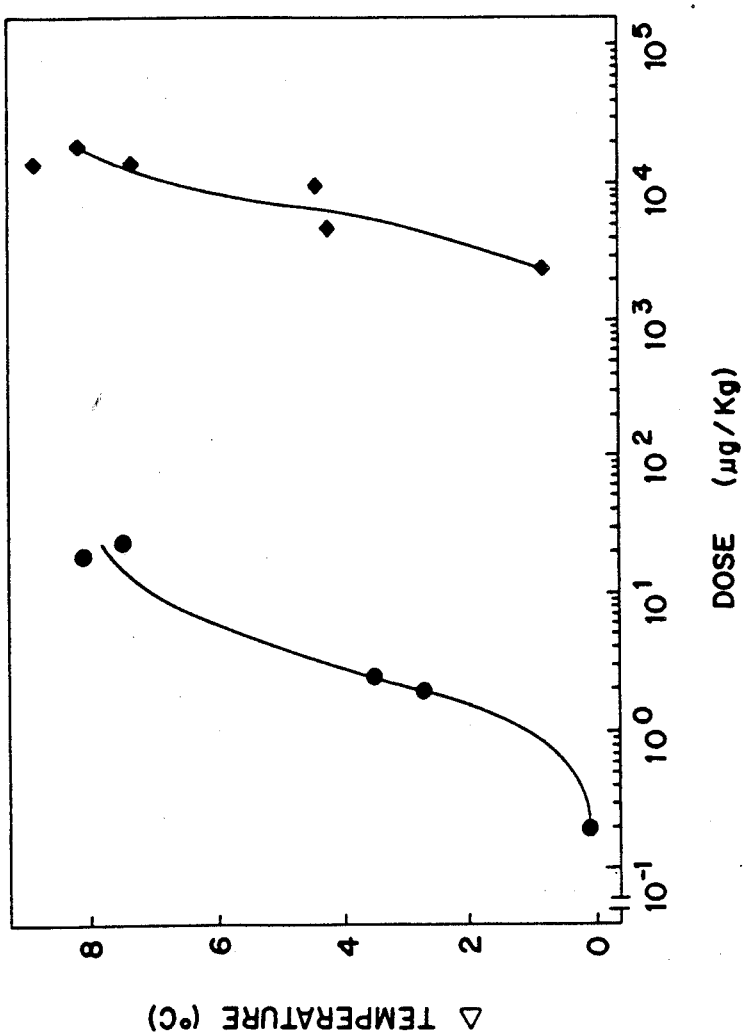
FIG. 9 shows the dose response curves for change in body temperature in mice.

Relative potencies of capsaicin and RTX are determined measuring the drop in body temperatures 1 hour after treatment. RTX has a 50% effective dose of 3 g/kg while capsaicin displays a 50% effective dose of 7 mg/kg as shown in FIG. 9. The drop in body temperature induced by both agents at maximally tolerated doses is approximately 8° C. When given intraperitoneally, capsaicin produces only transient effects and then only at doses higher than those required upon subcutaneous administration. Results obtained with RTX appear independent of administration route (see FIGS. 8 and 10).

Figure 10:
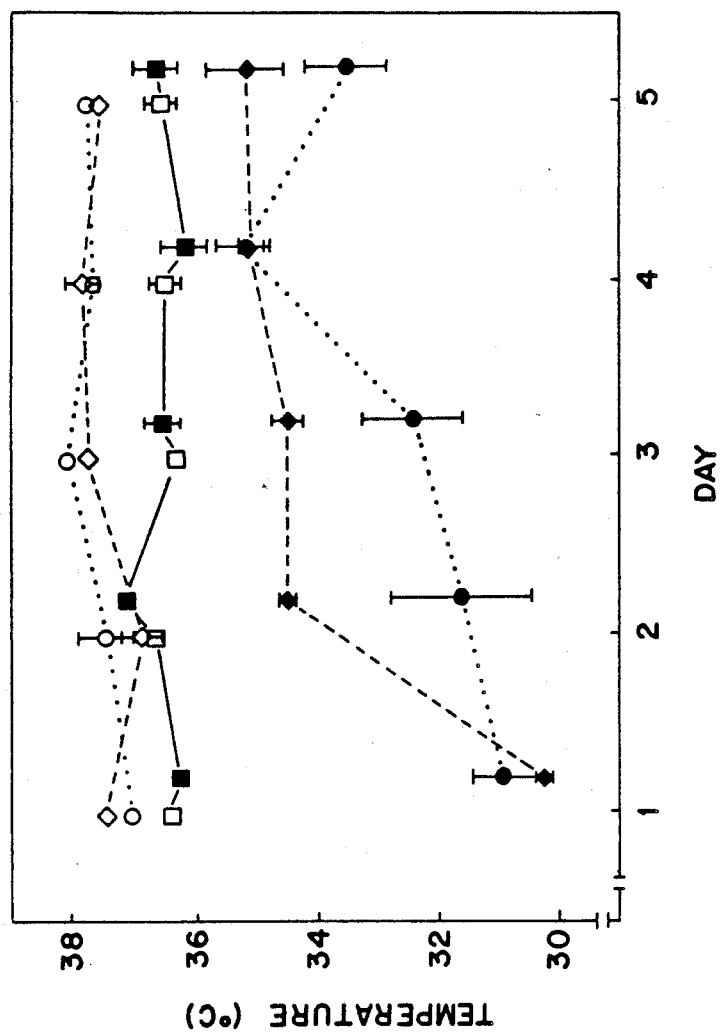
FIG. 10 shows the effect of repeated treatment with RTX or capsaicin on body temperature in mice.

Marked tolerance to the hypothermic effects of capsaicin develops by the second day of treatment as shown in FIG. 10. Tolerance also develops to RTX although over a longer period of time. Exposure to either drug appears to produce a resting state of hyperthermia of approximately 1.5° C. Following 4 days of treatment with either capsaicin or RTX, the hypothermic response of the animals to the other compound is examined (FIG. 10). The capsaicin pre-treated animals are comparably tolerant to RTX; the RTX pre-treated animals are partially tolerant to capsaicin.

Discussion

RTX and capsaicin share a capacity to dramatically depress the rectal temperature of mice. This effect may in part be due to the irritant/vasodilatory action of both compounds, contributing to enhanced heat loss. In addition, the application of capsaicin to discreet areas of the brain has strongly argued for a central site of action of this compound on thermoregulation (Monsereenusorn, Y., Kongsamut, S. and Pezalla, P. D. (1982) *CRC Crit. Rev. Toxicol.*, Vol. 10, pp. 321-339). The rapidity and degree of hypothermia induced by RTX may also argue for a central site of action.

Capsaicin has been reported to potently interact with the hepatic microsomal drug-metabolizing system and to irreversibly bind to microsomasl proteins (Miller, M. S., Brendel, K., Burks, T. F. and Sipes, I. G. (1983) *Biochem. Pharmacol.*, Vol. 32, pp. 547-551). Susceptibility to biotransformation may explain the relatively short duration of action of capsaicin and its lack of potency when administered intraperitoneally.

The mechanism by which tolerance develops to the effects of these hypothermic agents probably involves some component of enhanced metabolic breakdown, particularly considering the interaction of capsaicin with drug-metabolizing systems described above. The observed elevation in resting temperature following initial exposure, noted here and described previously for capsaicin in the rat (Jancso-Gabor, A., Szolcsanyi, J. and Jancso, N. (1970) *J. Physiol.*, Vol. 208, pp. 449-459; Szikszay, M. et al, (1982) *Naunyn-Schmiedeberg's Arch. Pharmacol.* Vol. 320, pp. 97-100) is indicative of some form of central response to the hypothermic stress and may contribute to the tolerance and cross-tolerance phenomena observed.

The remarkable potency of RTX as both an irritant and hypothermic agent indicates its potential as a pharmacological tool. Elucidation of the mechanism of action of capsaicin has been hampered by the relatively modest potency of this drug. Comparisons between the actions of RTX and capsaicin in various other paradigms may prove fruitful in delineating the mechanisms of these interesting natural products.

The figures of Example 2 are described in greater detail hereinbelow.

FIG. 8 shows the body temperatures in mice as a function of time after administration at time "O" of vehicle (■), 20 μg/kg RTX (●) or 15 mg/kg capsaicin (◆) subcutaneously. Each data point is the mean value from 4 animals ±s.e.m.

FIG. 9 shows the dose response curves for change in body temperatures 1 hour after treatment with RTX (●) or capsaicin (◆). RTX was administered i.p.(intraperitoneally); capsaicin was administered s.c. Each point represents the difference between mean values pre-and post-treatment for 2-4 animals in five individual experiments.

FIG. 10 shows the effect of repeated treatments with RTX or capsaicin on body temperature. Values represent the mean and s.e.m. of values obtained from 4 animals injected s.c. Body temperatures are measured before (□,○,◇) and one hour after (■,●,◆) treatment. Vehicle control (□, ■ ). Treatment with RTX (0, o) at a rate of 20 μg/kg on days 1 and 2 and 40 μg/kg on days 3 and 4. On day 5 cross-tolerance is examined by injection of 15 mg/kg capsaicin. Treatment with capsaicin ◇,◆) at a dose of 15 mg/kg on days 1 and 2 and 30 mg/kg on days 3 and 4. On day 5 cross-tolerance is examined by injection of 20 μg/kg RTX.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for desensitizing a subject animal, which comprises administering to said subject animal a therapeutically effective desensitizing amount of resiniferatoxin for desensitizing the subject to neurogenic inflammation, to chemically and thermally induced pain, to responses involving sensory afferent pathways sensitive to capsaicin or to responses involving the hypothalamic temperature control region.

2. The method of claim wherein the resiniferatoxin is administered topically, subcutaneously or intraperitoneally.

3. The method of claim 1, wherein resiniferatoxin is administered in the range of $1 \times 10^{-5}$ mg/kg to $5 \times 10^{-2}$ mg/kg to the subject.

4. The method of claim 1, wherein the subject is a mammal.

5. The method of claim 4, wherein the subject mammal is mouse, rat, domestic animal, or human.

6. The method of claim 5, wherein the domestic animal is a dog, cat, horse, cow, pig, goat or sheep.

7. The method of claim 1, wherein the resiniferatoxin is administered by single or multiple application.

8. The method of claim 1, which comprises administering to said subject animal a therapeutically effective desensitizing amount of resiniferatoxin for desensitizing the subject to neurogenic inflammation.

9. The method of claim 1, which comprises administering to said subject animal a therapeutically effective desensitizing amount of resiniferatoxin for desensitizing the subject to chemically and thermally induced pain.

10. The method of claim 1, which comprises administering to said subject animal a therapeutically effective desensitizing amount of resiniferatoxin for desensitizing the subject to responses involving sensory afferent pathways sensitive to capsaicin.

11. The method of claim 1, which comprises administering to said subject animal a therapeutically effective desensitizing amount of resiniferatoxin for desensitizing the subject to responses involving the hypothalamic temperature control region.

* * * * *